United States Patent [19]

Knox et al.

[11] Patent Number: 5,247,083
[45] Date of Patent: Sep. 21, 1993

[54] DIRECT ESTERIFICATION OF MYCOPHENOLIC ACID

[75] Inventors: Martin Knox; Gregory Donegan; Dennis A. Smith, all of Co Clare, Ireland

[73] Assignee: Syntex (U.S.A.) Inc., Palo Alto, Calif.

[21] Appl. No.: 993,146

[22] Filed: Dec. 18, 1992

Related U.S. Application Data

[63] Continuation-in-part of Ser. No. 911,635, Jul. 10, 1992, abandoned.

[51] Int. Cl.⁵ ............................................. C07D 413/12
[52] U.S. Cl. ..................................................... 544/153
[58] Field of Search ........................................ 544/153

[56] References Cited

U.S. PATENT DOCUMENTS 4,753,935  6/1988  Nelson et al. .................... 514/233.5

OTHER PUBLICATIONS

Wagner and Zook, *Synthetic Organic Chemistry*, (1953) pp. 480-481.
Morrison and Boyd "Organic Chemistry", Allyn & Bacon, Fifth Edition, Newton, Mass., pp. 841-843, 872-874. (1984).

*Primary Examiner*—Robert W. Ramsuer
*Attorney, Agent, or Firm*—Cathleen Desjardins; David A. Lowin; Tom M. Moran

[57] ABSTRACT

Mycophenolate mofetil is made non-catalytically by refluxing mycophenolic acid with 2-morpholinoethanol in an inert organic solvent capable of azeotropic removal of water.

23 Claims, No Drawings

DIRECT ESTERIFICATION OF MYCOPHENOLIC ACID

CROSS-REFERENCE TO RELATED APPLICATION

This is a continuation-in-part of pending application Ser. No. 07/911,635, filed Jul. 10, 1992, incorporated herein by reference, now abandoned.

FIELD OF THE INVENTION

The present invention relates to improved synthetic methods for making mycophenolate mofetil.

BACKGROUND INFORMATION

Mycophenolate mofetil is the morpholinoethyl ester of mycophenolic acid; it has the following formula.

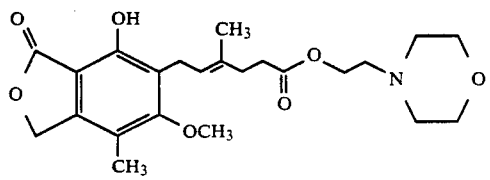

Mycophenolate mofetil, the pharmaceutically acceptable salts thereof, and the immunosuppressive, anti-inflammatory, anti-tumor and anti-viral uses thereof are described in U.S. Pat. No. 4,753,935 ("the '935 Patent"), incorporated herein by reference.

An acid halide condensation route for synthesizing mycophenolate mofetil has been described in the '935 Patent. This synthetic method suffered from various deficiencies. The acid halide condensation route required a two-step process and necessitated the use of three (3) molar equivalents of 2-morpholinoethanol to give a yield of 85% mycophenolate mofetil, which included the formation of a dimeric impurity (2%), among others, requiring a recrystallization step. Color problems with the finished product were also associated with this synthetic method due to trace iron contamination considered secondary to corrosive conditions caused by thionyl chloride in the acid chloride step.

A carbodiimide route described in the '935 Patent has proven impractical for the synthesis of pharmaceutical grade mycophenolate mofetil due to an unacceptable percentage of impurities in the final product.

Those skilled in the field of esterification reactions will appreciate that the conventional teachings for synthesis of an ester through the reaction of an acid and an alcohol has required the use of a catalyst to achieve acceptable yields. See, for example, Morrison & Boyd "Organic Chemistry", Allyn and Bacon, Fifth Edition, pp. 841–843, 872–874. Catalytic reactions, however, entail the added cost of the catalyst and the additional steps of its addition and separation from the reaction mixture.

Thus, a non-catalytic alternative for synthesizing mycophenolate mofetil has been desired. It has surprisingly been discovered that good yields of mycophenolate mofetil can be obtained without the disadvantage of the prior described methods and without the use of a catalyst. Moreover, it has unexpectedly been discovered that the reaction of mycophenolic acid and 2-morpholinoethanol gives at least the equivalent or increased yields by omitting the use of a catalyst (i.e., use of a traditional catalyst does not increase or even slows the reaction). These, and other aspects of the present invention are described in greater detail below in the Summary and Detailed Description of the Invention.

SUMMARY OF THE INVENTION

One aspect of the present invention concerns methods of making mycophenolate mofetil, by refluxing mycophenolic acid with 2-morpholinoethanol in an inert organic solvent capable of azeotropic removal of water.

Another, and a preferred aspect of the invention relates to a process for making mycophenolate mofetil, by refluxing mycophenolic acid and 2-morpholinoethanol in an inert organic solvent selected from the group consisting of toluene, xylene, benzene, mineral spirits and methylene chloride, or a mixture of solvents selected from the group consisting of toluene, xylene, benzene, mineral spirits and methylene chloride. Particularly preferred are toluene, xylene and the mixture of toluene and xylene.

DETAILED DESCRIPTION OF THE INVENTION

Definitions and General Parameters

The following definitions are set forth to illustrate and define the meaning and scope of the various terms used to describe the invention herein.

As used herein, the term "q.s." means adding a quantity sufficient to achieve a stated function, e.g., to bring a solution to the desired volume (i.e., 100%).

As used herein, the term "inert organic solvent" means a solvent inert under the conditions of the reaction being described in conjunction therewith. The inert organic solvents of the present invention must be capable of azeotropic removal of water; they include, for example, toluene, xylene, benzene, mineral spirits, methylene chloride and mixtures thereof. Particularly preferred are toluene, xylene and the mixture of toluene and xylene. Unless specified to the contrary, the solvents used in the reactions of the present invention are inert organic solvents.

As used herein, the term "reaction time" or "reflux time" means the time period in which the indicated chemical reaction takes place.

As used herein, the term "reaction pressure" means the atmospheric pressure present for the reaction mixture which may be affected by the elevation of the facility (e.g., at sea level or at 5400 feet), environmental conditions (e.g., weather conditions), or a reaction vessel system in which the system pressure can be controlled (as opposed to an open system) as well as remaining reaction parameters (e.g., temperature and volume).

As used herein, the term "pot temperature" means the temperature of the reaction mixture in which the chemical reaction takes place.

Unless specified to the contrary, the ranges of molar equivalents, reaction time, temperature, solute concentration, and atmospheric pressure described herein are approximate. For example, the phrases: 1) "using an excess (between 1.01 to 10 molar equivalents)"; 2) "a reaction time of 8 to 200 hours"; 3) "an initial pot temperature range of 30° to 145° C."; 4) "with a ratio of MPA to solvent of 1 gm:1 ml to 1 gm:10 ml"; 5) "at 0.03 to 3 atmospheres of pressure"; and 6) "the reaction completion is 80 to 100%" are respectively intended to mean 1) "using an excess (between about 1.01 to about 10 molar equivalents)"; 2) "a reaction time of about 8 to about 200 hours"; 3) "an initial pot temperature range of about 30° to about 145° C."; 4) "with a ratio of MPA to solvent of about 1 gm:1 ml to about 1 gm:10 ml"; 5) "at about 0.03 to about 3 atmospheres of pressure"; and 6) "the reaction completion is about 80 to about 100%."

Isolation and purification of the compound described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of Mycophenolate Mofetil

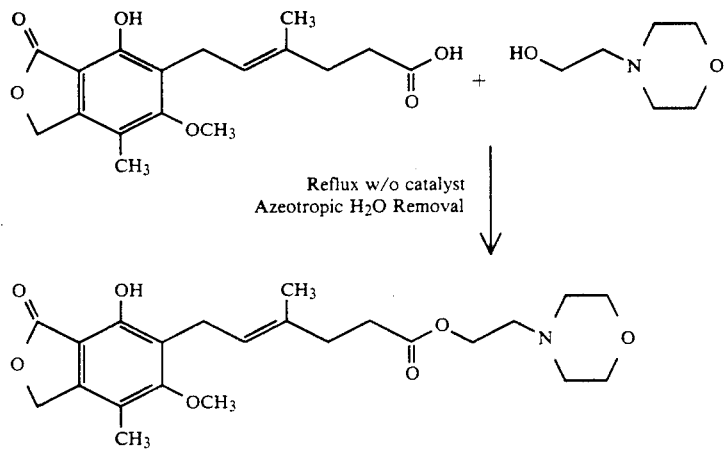

Starting Materials

Mycophenolic acid ("MPA") is widely commerically available, e.g., from Calbiochem Corporation, Fluke Chemie AG, Indofine Chemical Company, Inc., and Sigma Chemical Company.

2-Morpholinoethanol [also named as 4-(2-hydroxyethyl) morpholine] is widely commerically available, e.g. from Atomergic Chemetals Corporation, Schwizerhall, Inc., Sigma Chemical Company, and T.C.I. America, Inc.

Inert organic solvents capable of efficient azeotropic removal of water include, for example, toluene, xylene, benzene, mineral spirits, and methylene chloride and are widely commercially available, e.g. from Aldrich Chemical Company, Inc., Sigma Chemical Company, and/or Sun Refining and Marketing Co., Inc.

Preparation of Mycophenolate Mofetil

Referring to Reaction Scheme 1, MPA is esterified slowly in a refluxing inert organic solvent capable of azeotropic removal of water (such as toluene, xylene, benzene, mineral spirits, methylene chloride, or mixtures thereof; preferably xylene or toluene or a mixture of xylene and toluene) using an excess (between 1.01 to 10 molar equivalents, and preferably, 1.01 to 1.4 molar equivalents) of 2-morpholinoethanol. The reaction takes place with a reaction time of 8 to 200 hours (preferably 14 to 150 hours). The reaction mixture is heated to reflux with an initial pot temperature range of 30° to 145° C. (preferably 35° to 140° C.) increasing to a final pot temperature range of 40° to 155° C. (preferably 40° to 150° C.). The ratio of MPA to solvent used is 1 gm:1 ml to 1 gm:10 ml (preferably 1 gm:1 ml to 1 gm:4 ml, and most preferably 1 gm:1 ml to 1 gm:3 ml). The reaction pressure is 0.03 to 3 atmospheres of pressure (preferably 0.1 to 1.5 atmospheres of pressure, and most preferably 0.7 to 1.1 atmospheres of pressure). The reaction completion is 80 to 100% (typically 91 to 97%, and most typically 92 to 94%), without unacceptable impurities in the final product, as measured by h.p.l.c. normalization when conducted at the most preferable solute concentration, reaction pressure, reaction time and pot temperatures for the solvent employed. Water generated by the reaction is removed azeotropically. Upon completion of the esterification, the percent of reaction completion is measured (e.g., by h.p.l.c. normalization) and the color of the solution remaining in the reaction vessel is observed. If the reaction is 100% complete to give a substantially pure white solution, the desired product is obtained by precipitation, cooling, filtering, washing and isolation under vacuum. If not, then decolorization and removal of the unwanted MPA is necessary, optionally followed by a second decolorization (if needed), after which the solution is cooled, filtered, washed and isolated under vacuum.

Toluene Reaction Conditions

With toluene as the solvent, the reaction takes place with only a slight excess (between 1.01 to 1.40 molar equivalents, and preferably, 1.05 to 1.06 molar equivalents) of 2-morpholinoethanol. The reaction time is 20 to 120 hours (preferably 50 to 100 hours, and most preferably 100 hours). The reaction mixture is heated to reflux with an initial pot temperature range of 114° to 120° C. (preferably 115° to 118° C., and most preferably 116° C.) increasing to a final pot temperature range of 118° to 130° C. (preferably 118° to 125° C., and most preferably 121° C.). The ratio of MPA to toluene used is 1 gm:1 ml to 1 gm:10 ml (preferably 1 gm:1 ml to 1 gm:4 ml, and most preferably 1 gm:2 ml). The reaction pressure is 0.1 to 1.5 atmospheres of pressure (preferably 0.7 to 1.1 atmospheres of pressure, and most preferably one atmosphere of pressure, e.g., the atmospheric pressure at a sea level manufacturing facility). The reaction completion is 80 to 100% (typically 92 to 98%, and most typically 95 to 96%) without unacceptable impurities in the final product, as measured by h.p.l.c. normalization. The final yield is about 85% when conducted at the most preferable solute concentration, reaction pressure, reaction time and pot temperatures.

Xylene Reaction Conditions

With xylene as the solvent, the reaction takes place with only a slight excess (between 1.01 to 1.40 molar equivalents, and preferably, 1.05 to 1.06 molar equivalents) of 2-morpholinoethanol. The reaction time is 30 to 65 hours (preferably 30 to 50 hours and most preferably 36 hours). The reaction mixture is heated to reflux with initial pot temperature range of 120° to 145° C. (preferably 125° to 140° C., and most preferably 128° C.) increasing to a final pot temperature range of 125° to 155° C. (preferably 130° to 150° C., and most preferably 137° C.). The ratio of MPA to xylene is of 1 gm:1 ml to 1 gm:10 ml (preferably 1 gm:1 ml to 1 gm:4 ml, and most preferably 1 gm/2.5 ml). The reaction pressure is 0.1 to 1.5 atmospheres of pressure (preferably 0.7 to 1.1 atmospheres of pressure, and most preferably 0.82 atmospheres of pressure, e.g., the atmospheric pressure at a high altitude manufacturing facility at about 5400 feet elevation). The reaction completion is 80 to 100% (typically 85 to 95%, and most typically 91 to 92%) without unacceptable impurities in the final product, as measured by h.p.l.c. normalization. The final yield is about 78% when conducted at the most preferable solute concentration, reaction pressure, reaction time and pot temperatures.

Mineral Spirits Reaction Conditions

With mineral spirits as the solvent, the reaction takes place with only a slight excess (between 1.01 to 1.40 molar equivalents, and preferably 1.01 to 1.35 molar equivalents, and most preferably 1.1 to 1.3 molar equivalents) of 2-morpholinoethanol. The reaction time is 20 to 120 hours (preferably 30 to 100 hours and most preferably 60 to 70 hours). The reaction mixture is heated to reflux with an initial pot temperature range of 114° to 145° C. (preferably 115° to 140° C, and most preferably 125° to 130° C.) increasing to a final pot temperature range of 118° to 180° C. (preferably 118° to 165° C., and most preferably 128° to 140° C.). The ratio of MPA to mineral spirits is 1 gm:1 ml to 1 gm:10 ml (preferably 1 gm:1 ml to 1 gm:4 ml, and most preferably 1 gm:2 ml). The reaction pressure is 0.1 to 1.5 atmospheres of pressure (preferably 0.7 to 1.1 atmospheres of pressure, and most preferably one atmosphere of pressure, e.g., the atmospheric pressure at a sea level manufacturing facility). The reaction completion is 80 to 100% (typically 91 to 97%, and most typically 93 to 95%) without unacceptable impurities in the final product, as measured by h.p.l.c. normalization. The final yield is about 80% when conducted at the most preferable solute concentration, atmospheric pressure, reaction time and pot temperatures.

Other Solvents Reaction Conditions

With benzene as the solvent, the reaction mixture is heated to reflux with an initial pot temperature range of 80° to 100° C. (preferably 80° to 85° C.) increasing to a final pot temperature range of 82° to 110° C. (preferably 82° to 90° C.).

With methylene chloride as the solvent, the reaction time is 100 to 200 hours (preferably 130 to 190 hours). The reaction mixture is heated to reflux with an initial pot temperature range of 30° to 45° C. (preferably 35° to 45° C.) increasing to a final pot temperature range of 40° to 47° C. (preferably 40° to 46° C.).

Mixture of Solvents Reaction Conditions

Mixtures of the inert organic solvents (e.g., benzene and toluene, xylene and benzene, xylene and mineral spirits, or xylene and toluene, preferably xylene and toluene) may be used as the solvent. With a 1:99 to 99:1 (preferably 25:72 to 75:25, and most preferably 50:50) mixture of toluene and xylene as the solvent, the reaction takes place with only a slight excess (between 1.01 to 1.40 molar equivalents, and preferably 1.01 to 1.35 molar equivalents, and most preferably 1.1 to 1.3 molar equivalents) of 2-morpholinoethanol. The reaction time is 20 to 120 hours (preferably 30 to 100 hours and most preferably 60 to 63 hours). The reaction mixture is heated to reflux with an initial pot temperature range of 114° to 145° C. (preferably 115° to 140° C., and most preferably 120° to 125° C.) increasing to a final pot temperature range of 118° to 155° C. (preferably 118° to 150° C., and most preferably 128° to 140° C.). The ratio of MPA to the mixture of xylene and toluene is 1 gm:1 ml to 1 gm:10 ml (preferably 1 gm:1 ml to 1 gm:4 ml, and most preferably 1 gm:2 ml). The reaction pressure is 0.1 to 1.5 atmospheres of pressure (preferably 0.7 to 1.1 atmospheres of pressure, and most preferably one atmosphere of pressure, e.g., the atmospheric pressure at a sea level manufacturing facility). The reaction completion is 80 to 100% (typically 91 to 97%, and most typically 92 to 94%) without unacceptable impurities in the final product, as measured by h.p.l.c. normalization. The final yield is about 80-85% when conducted at the most preferable solvent ratio, solute concentration, atmospheric pressure, reaction time and pot temperatures.

Effect of Catalysts on the Reaction

The effects of acid and base catalysts, such as toluene sulfonic acid, sulfuric acid, triethylenediamine and triethylamine, can be determined by repeating the reaction under identical conditions both with and without a catalytic amount (e.g., 0.1 molar equivalent) of the acid or base catalyst. Experimental tests show that the addition of acidic or basic catalysts to the above process resulted in no increase in the reaction completion or final yield of the mycophenolate mofetil synthesis. Thus it is preferred to carry out the process of the present invention with no catalyst.

Preparation of the Salts of Mycophenolate Mofetil

The salts of mycophenolate mofetil can be prepared, starting with the free acid as made by the present invention in accordance with Reaction Scheme 1, by following the teachings of U.S. Pat. No. 4,753,935, for example at Column 6, Lines 10-36, incorporated herein by reference.

Preferred Processes and Last Steps

Mycophenolate mofetil can be prepared according to the following preferred last steps:

MPA and a slight excess (1.05 molar equivalents) of 2-morpholinoethanol are refluxed in toluene with a ratio of MPA to toluene of 1 gm/2 ml, using no catalyst, for a reaction time of 100 hours at an initial pot temperature of 116° C. increasing to a final pot temperature of 121° C. at one atmosphere of pressure; or MPA and a slight excess (1.06 molar equivalents) of 2-morpholinoethanol are refluxed in xylene with a ratio of MPA to xylene of 1 gm/2.5 ml, using no catalyst, for a reaction time of 36 hours at an initial pot temperature of 128° C. increasing to a final pot temperature of 137° C. at 0.82 atmospheres of pressure; or MPA and a slight excess (1.20 molar equivalents) of 2-morpholinoethanol are refluxed in a 50:50 mixture of toluene and xylene as solvent with a ratio of MPA to solvent of 1 gm/2 ml, using no catalyst, for a reaction time of 63 hours at an initial pot temperature of 125° C. increasing to a final pot temperature range of 130°–140° C. at one atmosphere of pressure.

EXAMPLES

The following examples are given to enable those skilled in the art to more clearly understand and to practice the present invention. They should not be considered as limiting the scope of the invention, but merely as being illustrative and representative thereof.

EXAMPLE 1

Synthesis of Mycophenolate Mofetil

A. Mixture of Toluene and Xylene As The Inert Organic Solvent

Using a 50:50 mixture of toluene and xylene as the inert organic solvent: mycophenolic acid (40 g, 0.125 moles) and a 50:50 mixture of toluene and xylene as solvent (40 ml) were warmed gently to form a solution. A slight excess (1.20 molar equivalents) of 2-morpholinoethanol (19.65 g, 0.15 moles) and the solvent (40 ml) were added. The reaction mixture was stirred for half an hour and then heated to reflux at an initial pot temperature of 125° C. (which increased four degrees to 129° C. during reflux) under a Dean-Stark trap for 63 hours. An h.p.l.c. completion check at 63 hours indicated: 1) the presence of 4.79% unreacted mycophenolic acid, and 2) 0.35% impurities, i.e., the reaction completion was 94.9%. The color of the solution was brown. The vessel and contents were cooled and 2.8 g of acid-washed carbon was added. The vessel was then heated to 90° C. and aged for 1 hour, after which time the product was filtered through a celite bed. The resulting solution was stripped until no more distillate was produced and the vessel was cooled to 50° C. Ethyl acetate (230 mls) was added and the solution was charged to a separatory funnel and washed with 68 mls of water, and then with 68 mls of a saturated solution of sodium bicarbonate four times. A final wash with 68 mls of water was given. The ethyl acetate was distilled off and the product was treated with 2.1 gm of silica gel for 1 hour at 50° C. Filtering and stripping out the ethyl acetate was done to give a total volume of 90 mls. This volume was held at 65° C. for 1 hour to dissolve all the product, was cooled to 42° C. and held at this temperature for 2.5 hours, and was finally cooled to −5° C. and aged at this temperature for 8 hours. The product was filtered and washed with 45 ml of cold ethyl acetate/SBP 65/70 (1:2 v/v). The product was dried under full vacuum at 60° C. for 3 hours until the weight loss was less than 1%. The final yield was 82.9%. There was 0.0% impurities in the isolated product. The product conformed to the infrared spectrum of a mycophenolate mofetil reference standard material.

B. Other Inert Organic Solvents

1) Toluene as Solvent a) By following the procedure of part A and substituting toluene for the mixture of toluene and xylene as the solvent, and refluxing the reaction mixture for 48 hours at an initial pot temperature of 118° C. which increased to 120° C. during reflux, a reaction completion check at 48 hours indicated: 1) the presence of 10.1% unreacted mycophenolic acid, and 2) 0.0% impurities, i.e., the reaction completion was 89.9% and the estimated yield based on the reaction completion was 79.1%.

b) Mycophenolic acid (7 g, 0.02 moles) and toluene (25 ml) were warmed gently to form a solution. A slight excess (1.05 molar equivalents) of 2-morpholinoethanol (3 g, 0.021 moles) and toluene (25 ml) were added. The reaction mixture was stirred for half an hour and then heated to reflux at an initial pot temperature of 117° C. (which increased a few degrees during reflux) under a Dean-Stark trap for 80 hours. An h.p.l.c. completion check at 80 hours indicated: 1) the presence of 10–15% unreacted mycophenolic acid, and 2) the absence of impurities, i e., the reaction completion was 85–90%; . The reaction mixture was cooled, washed with water (2×15 ml), 10% aqueous sodium bicarbonate (2×15ml) and finally with water (15 ml). The toluene layer was stripped to a volume of about 20 ml in vacuo, n-hexane (30 ml) was added and the resulting slurry aged at room temperature for 2 hours. The product was filtered, washed with n-hexane (ca. 10 ml) and dried in vacuo at 60° C. The yield was 7.9 g (83%) of mycophenolate mofetil. The product conformed to the infrared spectrum of a mycophenolate mofetil reference standard material.

2) Xylene as Solvent

By following the procedure of part B(1)(b) and substituting xylene (8.25 ml) for each volume of toluene (25 ml), using an excess of 1.06 molar equivalents of 2-morpholinoethanol (3.03 g, 0.0212 moles) and refluxing the reaction mixture for 36 hours at an initial pot temperature of 128° C. which increased to 137° C. during reflux at 0.82 atmospheres of pressure, a reaction completion of 91–92% and the absence of impurities were determined by h.p.l.c. normalization, with a final yield of about 78% mycophenolate mofetil.

3) Mineral Spirits as the Solvent

By following the procedure of part A and substituting Mineral Spirits (120/160) for the mixture of toluene and xylene as the solvent, and refluxing the reaction mixture at an initial pot temperature of 128° C. which increased to 132° C. during reflux, a reaction completion check at 63 hours indicated: 1) the presence of 4.4% unreacted mycophenolic acid, and 2) 1.5% impurities, i.e., the reaction completion was 94.1% and the estimated yield based on the reaction completion was 82.8%.

C. Other Reaction Parameters

By following the procedure of part B(1)(b), but using an excess of 1.1 molar equivalents of 2-morpholinoethanol (3.3 g, 0.0231 moles) and refluxing the reaction mixture for 24 hours at an initial pot temperature of 114° C. which increased several degrees during reflux, a reaction completion of 72% and the absence of impurities were determined by h.p.l.c. normalization.

EXAMPLE 2

Synthesis of Mycophenolate Mofetil Reacting Mycophenolic Acid With 2-Morpholinoethanol Using A Catalyst A. By following the procedure of Example 1, part A and by adding sulfuric acid (at 0.1 molar equivalent of MPA) to the reaction mixture prior to refluxing, a reaction completion check at 63 hours indicated: 1) the presence of 5.7% unreacted mycophenolic acid, and 2) 0.82% impurities, i.e., the reaction completion was 93.5%. The final yield was 77.9%. There was 0.4% impurities in the isolated product.

B. By following the procedure of Example 1, part A and by adding triethylenediamine (at 0.1 molar equivalent of MPA) to the reaction mixture prior to refluxing, a reaction completion check at 63 hours indicated: 1) the presence of 2.5% unreacted mycophenolic acid, and 2) 13.4% impurities, i.e., the reaction completion was 84.1%. The final yield was 76.5%. There was 7.5% impurities in the isolated product.

C. By following the procedure of Example 1, part C and by adding triethylamine (at 0.1 molar equivalent of MPA) to the reaction mixture prior to refluxing, a reaction completion of 70% and the absence of impurities were determined by h.p.l.c. normalization.

D. By following the procedure of Example 1, part C and by adding toluene sulfonic acid (at 0.1 molar equivalent of MPA) to the reaction mixture prior to refluxing, a reaction completion of 67% and the absence of impurities were determined by h.p.l.c. normalization.

EXAMPLE 3

Synthesis of Mycophenolate Mofetil

Reacting Mycophenolic Acid With
2-Morpholinoethanol Under Reduced Pressure

A. By following the procedure of Example 1, part A and by reducing the pressure to about 290 mm of Hg (about 0.4 Atmospheres), a reaction completion check at 63 hours indicated: 1) the presence of 21.9% unreacted mycophenolic acid, and 2) 0.7% impurities, i.e., the reaction completion was 77.4%. The final yield was 61.3%. There was 0.3% impurities in the isolated product.

B. By following the procedure of Example 1, part B(1)(a) and by reducing the pressure to about 290 mm Hg (about 0.4 Atmospheres), a reaction completion check at 48 hours indicated: 1) the presence of 32.1% unreacted mycophenolic acid, and 2) 0.63% impurities, i.e., the reaction completion was 67.3% and the estimated yield based on the reaction completion was 59.2%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A process for making mycophenolate mofetil consisting essentially of refluxing mycophenolic acid with 2-morpholinoethanol in an inert organic solvent capable of azeotropic removal of water, starting at an initial pot temperature of at least about 30° C.

2. The process of claim 1 wherein said solvent is:
   selected from the group consisting of toluene, xylene, benzene, mineral spirits and methylene chloride, or
   a mixture of solvents selected from the group consisting of toluene, xylene, benzene, mineral spirits and methylene chloride.

3. The process of claim 2 wherein about 1.01 to about 1.40 molar equivalents of 2-morpholinoethanol is used.

4. The process of claim 3 wherein said solvent is toluene.

5. The process of claim 4 wherein the pot temperature increases from an initial range of about 114° C. to about 120° C. to a final range of about 118° C. to about 130° C.

6. The process of claim 5 wherein the reflux time ranges from about 50 to about 100 hours.

7. The process of claim 6 wherein the reflux time is about 100 hours.

8. The process of claim 7 wherein the ratio of mycophenolic acid to toluene is about 1 gm/2 ml.

9. The process of claim 8 wherein about 1.05 molar equivalents of 2-morpholinoethanol is used.

10. The process of claim 3 wherein said solvent is xylene.

11. The process of claim 10 wherein the pot temperature increases from an initial range of about 120° C. to about 145° C. to a final range from about 125° C. to about 155° C.

12. The process of claim 11 wherein the reflux time ranges from about 30 to about 65 hours.

13. The process of claim 12 wherein the reaction pressure is about 0.82 atmospheres.

14. The process of claim 13 wherein the ratio of mycophenolic acid to xylene is about 1 gm/2.5 ml.

15. The process of claim 14 wherein about 1.06 molar equivalents of 2-morpholinoethanol is used.

16. The process of claim 3 wherein said solvent is a 50:50 mixture of toluene and xylene.

17. The process of claim 16 wherein the pot temperature increases from an initial range of about 114° C. to about 145° C. to a final range of about 118° C. to about 155° C.

18. The process of claim 17 wherein the reflux time ranges from about 30 to about 100 hours.

19. The process of claim 18 wherein the pot temperature increases from an initial range of about 120° C. to about 125° C. to a final range of about 128° C. to about 140° C.

20. The process of claim 19 wherein the reflux time is about 60 to 63 hours.

21. The process of claim 20 wherein the ratio of mycophenolic acid to the 50:50 toluene and xylene mixture is about 1 gm/2 ml.

22. The process of claim 21 wherein about 1.1 to 1.3 molar equivalents o 2-morpholinoethanol is used.

23. A process for making mycophenolate mofetil consisting essentially of refluxing mycophenolic acid with 2-morpholinoethanol in an inert organic solvent capable of azeotropic removal of water selected from the group: xylene, toluene, and mixtures of xylene and toluene, starting at an initial pot temperature of at least about 114° C.

* * * * *